(12) United States Patent
Zhang et al.

(10) Patent No.: US 7,799,204 B2
(45) Date of Patent: Sep. 21, 2010

(54) VOLTAMMETRIC ION SENSOR

(75) Inventors: Jie Zhang, Victoria (AU); Alan Maxwell Bond, Victoria (AU); Alexander Richard Harris, Victoria (AU)

(73) Assignee: Oxford Biosensors Limited, Oxfordshire (GB)

( * ) Notice: Subject to any disclaimer, the term of this patent is extended or adjusted under 35 U.S.C. 154(b) by 394 days.

(21) Appl. No.: 11/665,107

(22) PCT Filed: Oct. 14, 2005

(86) PCT No.: PCT/GB2005/003988

§ 371 (c)(1),
(2), (4) Date: Apr. 10, 2007

(87) PCT Pub. No.: WO2006/040588

PCT Pub. Date: Apr. 20, 2006

(65) Prior Publication Data

US 2008/0011606 A1    Jan. 17, 2008

(30) Foreign Application Priority Data

Oct. 15, 2004  (GB) ................................ 0423025.6

(51) Int. Cl.
*G01N 27/333* (2006.01)
*G01N 27/403* (2006.01)

(52) U.S. Cl. ....................... 205/789; 204/416; 204/418; 205/789.5

(58) Field of Classification Search ................. 204/416, 204/405, 418, 433; 205/789, 787.5, 775, 205/792.5, 789.5
See application file for complete search history.

(56) References Cited

U.S. PATENT DOCUMENTS

| 5,286,365 | A | 2/1994 | Shu |
| 5,964,994 | A | 10/1999 | Craig et al. |
| 7,504,019 | B2 * | 3/2009 | Forrow et al. ............. 205/777.5 |
| 2004/0176672 | A1 * | 9/2004 | Silver et al. ................. 600/345 |

FOREIGN PATENT DOCUMENTS

| GB | 2185821 A | | 7/1987 |
| JP | 59-119254 | | 7/1984 |
| WO | WO 03/012417 | * | 2/2003 |
| WO | WO 03/012417 A2 | | 2/2003 |

OTHER PUBLICATIONS

Johnson et al. (Ionophore-based ion-selective potentiometric and optical sensors, Anal Bioanal Chem (2003) 376: 328-341).*

(Continued)

*Primary Examiner*—Alexa D Neckel
*Assistant Examiner*—Jennifer Dieterle
(74) *Attorney, Agent, or Firm*—Quarles & Brady LLP

(57) ABSTRACT

A method and device for the quantitative determination of an ion in a fluid which comprises subjecting the fluid to voltammetry using a sensing electrode which comprises an electrically conducting support having a surface which is coated with a support matrix, the support matrix containing an electroactive species capable of being oxidised or reduced to form a charged species, and an ionophore.

20 Claims, 6 Drawing Sheets

OTHER PUBLICATIONS

Zhang et al. (Voltammetric Studies with Adhered Microparticles and the Detection of a Dependence of Organometallic Cis+ f Trans+ First-Order Isomerization Rate Constants on the Identity of the Ionic Liquid, J. Phys. Chem. B 2004, 108, 7363-7372).*

Allen et al., Crown Ether Derivatives of Anthraquinone as Ionophores in Ion-Selective Electrodes, Electroanalysis, 4, 1992, 533-537.*

T. Wooster et al., An Analogy Of An Ion-Selective Electrode . . . , 75 Analytical Chemistry 586-592 (2003).

D.L. Coffen et al., Tetrathioethylenes, 93 J. American Chemical Society 2258-2268 (1971).

W. Rhee et al., Lithium 1,1-Dicyclopentadienyl-1-bromo-2,3,4,5-tetraphenylstannnole . . . , 97 J. American Chemical Society 2291-2293 (1975).

F. Kaufman et al., Electrochemical Preparation And Control of Stoichiometry . . . 98 J. American Chemical Society 1596-1597 (1976).

J. Jiang et al., Electrochemical Crystallisation and Characterisation of Platinum . . . 114 Synthetic Metals 209-218 (2000).

A. Ellern et al., A New Polymorphic Modification Of Tetrathiafulvalene . . . , 6 American Chemical Society 1378-1385 ( 1994.

L. Abouderbala et al., Anion Sensing 'Venus Flytrap' Hosts: A Modular Approach, Chemical Community 358-359 (2002).

L. Abouderbala et al., Cooperative Anion Binding And Electrochemical Sensing . . . , 99 Proc. Natl. Acad. Sci. USA 5001-5006 (2002).

R. Gulaboski et al., An Electrochemical Method For Determination Of The Standard . . . , 4 Electrochemistry Communications 277-283 (2002).

R. Gulaboski et al., Standard Gibbs Energies Of Transfer Of Halogenate . . . , 5 Phys. Chem. Chem. Phys., 1284-1289 (2003).

D. Henn et al., Voltammetric Ion-Selective Electrodes (VISE), 12 Electroanalysis 1263-1271 (2000).

J. Koryta, Electrochemical Polarization Phenomena At The Interface . . . , 24 Electrochemica Acta 293-300 (1979).

K. Cammann et al., New Sensing Principles For Ion Detection, 35-36 Sensors And Actuators B 26-31 (1996).

F. Scholz et al., The Determination Of Standard Gibbs Energies Of Transfer Of Cations . . . , 5 Electrochemistry Communications 929-934 (2003).

S. Nishizawa et al., Hydrogen-Bond Forming Ionophore For Highly Efficient Transport . . . , 128 Analyst 663-669 (2003).

V. Mirceski et al., Determination Of The Standard Gibbs Energies Of Transfer Of Cations . . . , 4 Electrochemistry Communications 814-819 (2002).

* cited by examiner (a)

(b)

VOLTAMMETRIC ION SENSOR

FIELD OF THE INVENTION

The present invention relates to a method of quantitatively and selectively measuring ionic materials in fluids. The invention also relates to a device and an electrode for carrying out such measurements.

BACKGROUND TO THE INVENTION

The most common method of quantitative and selective detection of ions has been by using ionophore based ion-selective electrodes (ISEs). The ionophore based ISE has been developed into a routine analytical technique in a wide range of fields since the 1960s. In this type of ISE, ionophore is dissolved in a polymer supported water immiscible organic solvent or plasticizer together with some other additives, such as organic supporting electrolyte (e.g. tetraheptylammonium (4-chlorophenyl) borate). Good selectivity is achieved mainly due to the specific ion binding process of ionophore. Under ideal conditions, the potential difference between the ISE and reference electrode, $\Delta E$, is mainly varied by the Donnan potential across the water/membrane interface which is mainly governed by the concentration of target ion in the aqueous phase.

In order to obtain a reliable measurement using an ISE, it is necessary to obtain an equilibrium state. This is achieved by inserting the ISE into the analyte fluid and allowing a period of a few minutes for the ion to be detected to migrate across the membrane to achieve equilibrium. The timescale of the measurement is therefore dictated by time to achieve equilibrium and is undesirably slow. Sensors having more rapid response times are therefore desired.

A further difficulty with known ISEs relates to the large sample size required for measurement. The minimum size of ISE which can be produced is limited by practical requirements. Accordingly, the measurement can only be carried out if a sufficient amount of sample fluid is present. It would be desirable, however, to provide an ion selective microelectrode which can operate with very small sample volumes.

Attempts have been made to address the problems of ionophore ISEs. For example, voltammetric sensors are known which are based on the principle of facilitated ion transfer across the interface of two immiscible electrolyte solutions. However, the selectivity of voltammetric sensors is not adequate and their use has not thus far been favoured over ionophore ISEs.

A new sensor is therefore required which addresses the problems associated with ionophore ISEs, and which provides a high selectivity.

SUMMARY OF THE INVENTION

The present invention addresses these difficulties in the provision of a new method for ion sensing with rapid response time, small sensor volume and high selectivity. Accordingly, the present invention provides a method for the quantitative determination of an ion in a fluid which comprises subjecting the fluid to voltammetry using a sensing electrode which comprises an electrically conducting support having a surface which is coated with a support matrix (e.g. a membrane), the support matrix containing an electroactive species capable of being oxidised or reduced to form a charged species, and an ionophore.

The present invention also provides a device for the quantitative determination of an ion in a fluid which comprises a sensing electrode according to the invention and one or more further electrodes. The device is for use in a voltammetric determination method.

The present invention also provides an electrode comprising an electrically conducting support having a surface which is coated with a support matrix (e.g. a membrane), the support matrix containing an electroactive species capable of being oxidised or reduced to form a charged species, and an ionophore.

The technology of the present invention can be applied to electrodes of any size or type. In one embodiment, the present invention therefore encompasses ion selective microelectrodes and accordingly provides a method of quantitatively detecting ions in low volume samples.

The devices of the present invention have response times which are significantly lower than ionophore ISEs known in the art. Therefore, a reliable measurement can typically be completed within about 10 seconds of applying a fluid to the electrode of the present invention.

Further, not only is the response time reduced, but the skilled person is provided with the ability to control the response time depending on the specific requirements of the test to be carried out. By altering the support matrix thickness, the response time of the device can be changed, and thus tailored to suit the application.

One embodiment of the invention, in which the electrochemical reaction is reversible, provides particularly accurate results. This is achieved by applying a scan of the potential to the sensing electrode and determining the potential at which the current peaks occur in both the cathodic and anodic scans. By averaging the two results, a more accurate measurement can be achieved. This is the mid point potential (Em). This embodiment also has the advantage that a reliable measurement can be made even before the system has fully reached chemical equilibrium.

The method of the invention therefore provides a rapid and reliable detection technique and, through the use of particular ionophores in the support matrix, can be highly selective for the particular ion to be detected. In addition, the presence of the support matrix retains the electroactive species and other substances at the electrode surface and helps to prevent dissolution in the fluid.

BRIEF DESCRIPTION OF THE FIGURES

In FIG. 7(a), cyclic voltammagrams are shown measured on a solution having NaCl concentrations of 1 mM (solid line), 10 mM (dashed line), 100 mM (dotted line) and 1000 mM (dotted and dashed line). FIG. 7(b) shows the sensitivity of a thin film with 20 mM Na ionophore VI at a scan rate of 100 mV s$^{-1}$ varying NaCl concentration. S=the gradient (slope) of the graph, R=correlation coefficient and SD=standard deviation.

DETAILED DESCRIPTION OF THE INVENTION

Figure 1:
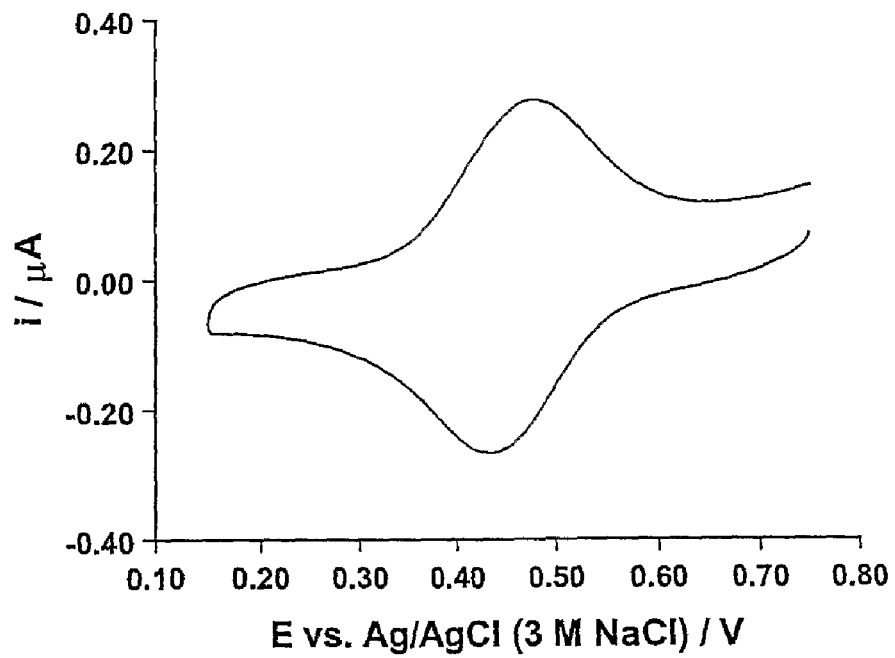
FIG. 1 depicts a voltammogram obtained using a $K^+$ sensor according to one embodiment of the invention.

The present invention is based on a process comprising two basic steps. These are illustrated below, using the example of tetracyanoquinodimethane (TCNQ) as an electroactive species, and a membrane as the support matrix.

1. Initial electrochemically induced redox reaction of electroactive species;

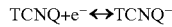

2. Movement of ions into the membrane to attain electrical neutrality (in other words to neutralize the electrochemically produced charge). Since, in the illustrated case, this charge is negative, cations (X$^+$) are incorporated (ingressed) into the membrane.

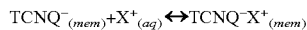

The incorporation of specific cations is provided by selection of a particular ionophore, which influences the free energy associated with each cation in the support matrix, with the result that the incorporation of a specific target cation is far more favorable than any others.

Sensing is based on measuring the potential (ΔE) of the electrochemical redox process relative to a reference system. This provides information relating to the free energy of ion transfer into the support matrix and hence information about the concentration of the target ion in the sample. Practically, a voltammetric scan is applied to the sensing electrode and the potential at which the peak current for the electroactive species occurs is measured. The position of this peak is dependent on the transfer of ions in/out of the support matrix, and thus on the concentration of ions in the fluid.

The sensing electrode of the invention comprises an electrically conducting support, the nature of which is not important. It will generally be made of metal or carbon and includes, for example, printed conductive electrodes formed by the incorporation of conductive media within a polymeric coating or ink. Suitable metals which can be used include silver, gold, platinum, copper and nickel, e.g. gold, platinum and nickel, as well as other metals that provide conductivity in the final electrode. Alternatively, conductive carbons can be particularly effective. These can either be in particulate form or in a graphitic form that typically possesses an aspect ratio. The electrode preferably has at least one dimension of less than 50 μm. The use of electrodes of this size enables measurements to be carried out on small sample volumes, for example as small as 1 μl.

The electrically conducting support has a surface which is coated with a support matrix (e.g. a membrane) containing, at least, an electroactive species and an ionophore. By the support matrix "containing" these species, we mean that the electroactive species and ionophore, and optionally other substances, are present within pores in the support matrix structure. Thus, the support matrix acts to entrap the electroactive species, ionophore and optionally other materials at the electrode surface. The support matrix containing at least an electroactive species and an ionophore is also referred to herein as the "support matrix phase" (or the "membrane phase" when the support matrix is a membrane).

The support matrix may be made from any material having a matrix structure which is capable of containing materials such as electroactive species and ionophores within the matrix structure. For example, the support matrix may be a membrane. Typically the support matrix is a polymeric material such as PVC, dielectric ink, polyethylene or polyester or any other suitable material which forms a water insoluble film. In one embodiment, the support matrix is a membrane of a polymeric material such as PVC. The thickness of the support matrix influences the response time of the device, with thinner matrices providing more rapid response times. The thickness of the support matrix can therefore be selected according to the response time that is required.

In one embodiment of the invention, a single layer of support matrix is used. In a further embodiment, the support matrix does not contain a fluorophore.

The electroactive species is capable of being oxidised or reduced to form a charged species. This means that either oxidation of the electroactive species may occur resulting in a charged product, or reduction of the electroactive species may occur resulting in a charged product. The electroactive species can be oxidized or reduced at the sensing electrode on application of a potential, thus causing the formation of a charged species in the support matrix phase. The build up of charge in the support matrix phase leads to the ingress/egress of counter ions from the aqueous phase into the support matrix phase.

Preferred electroactive species are hydrophobic, more preferably both oxidized and reduced forms of the electroactive species are hydrophobic. This helps to retain the electroactive species within the support matrix and to prevent leakage into the fluid, which is typically aqueous. It is further preferred that the electroactive substance undergoes reversible electrochemistry as this enables more accurate measurement to be made. The electroactive species should also preferably be chemically stable when entrapped within the support matrix.

Examples of suitable electroactive species are the compounds sometimes referred to as synmetals. Preferably the electroactive species is a semi-conductor. In particular, species containing various cyano carbons in which a substantial portion of the functionality consists of cyano groups are suitable for detecting cations. As a consequence of the large number of cyano groups, the cyano carbons are highly reactive electrophilic molecules. Specific examples which may be used in the present invention include tetracyanoethylenes, tetracyanoquinodimethanes (TCNQ), N,N'-dicyano-p- quinodiimine (DCNQI) and N,7,7-tricyanoquinomethanimines. The analogues (any quinine) and the many derivatives of these can also be used including halogenated e.g. fluorinated derivatives such as tetracyanotetrafluoroquinodimethane, and alkylated e.g. methylated derivatives such as tetracyanoquinoethylene (TCNE) and 2,4,6,8-tetracyanoazulene as well as analogues including other quinoid compounds such as 2,3-dichloro-5,6-dibenzo-1,4-quinone. Species suitable for detecting anions include tetrathiafulvalene (TTF), tetrathiafulvalene analogues and derivatives thereof including alkylated derivatives, for example, methyl substituted derivatives such as tetramethyltetrathiafulvalene (TMTTF), as well as ethylene and methylene derivatives such as bis (ethylenedithio)tetrathiafulvalene (ET) and bis-(methylenedithio)tetrathiafulvalene (BMDT-TTF), including the corresponding selenium or other hetero atom compounds. Other species which can be used include the fullerene family including $C_{60}$, $C_{70}$, $C_{76}$ and $C_{84}$ fullerenes. Other species which can be used include phthalocyanines such as platinum phthalocyanine and certain tellurium derivatives such as:

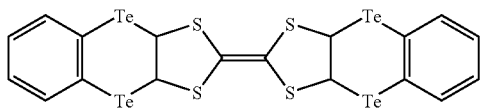

Further details can be found in, for example, J. Am. Chem. Soc. 93, 2258 (1971), 97, 2291 (1975) and 98, 1596 (1976), Synth. Met. 114, 209 (2000) and Chem. Mater. 6 1378 (1994) and the like.

Preferred examples of electroactive species include decamethylferrocene (DMFc), 1,1'-dimethylferrocene (DiMFc) and 7,7,8,8-tetracyanoquinodimethane (TCNQ).

In one embodiment of the invention, the electroactive species is not phthalocyanine or a phthalocyanine derivative.

The ionophore may be any ionophore which is known for use with ionophore ISEs. Typical examples include valinomycin, dibenzo-18-crown-6 (DB18C6), bis[(benzo-15-crown-4)-4'-ylmethyl]pimelate and [2-dodecyl-2-methyl-1,3-propanediyl-bis[N-5'-nitro(benzo-15-crown-5)-4'-yl) carbamate]](BME44), for example valinomycin or dibenzo-18-crown-6 (DB18C6), for $K^+$ sensors; bis[(12-crown-4) methyl]dodecylmethylmalonate or 4-tert-butylcalix[4]arene-tetraacetic acid tetraethylester, for example bis[(12-crown-4) methyl]dodecylmethylmalonate, for $Na^+$ sensors; and [4,5-dimethyl-3,6-dioctyloxy-1,2-phenylen]-bis-(mercury-trifluoroacetate) (ETH 9009), trichlorohexyltin chloride, tridodecylmethylammonium chloride and modular podand, 1,3,5-tris(3-((ferrocenylmethyl)amino)pyridiniumyl)-2,4,6-triethylbenzene hexafluorophosphate ([PD][PF$_6$]$_3$) for $Cl^-$ sensors. As a further example, N,N,N',N'-tetracyclo-3-oxapentanediamide (ETH129) can be used for $Ca^{2+}$ sensors.

However, alternative ionophores which are selective for these or other ions can also be used. The majority of the above mentioned ionophores are commercially available. [PD] [PF$_6$]$_3$ can be manufactured by the technique described by Abouderbala et al (Chem. Commun. 2002, 358 and Proc. Natl. Acad. Sci. USA 2002, 99, 5001).

The structures of some of the exemplified ionophores are as follows:

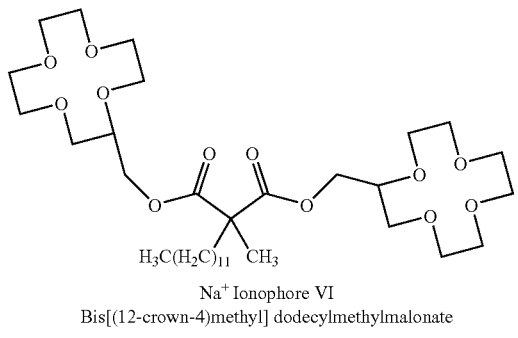

Na$^+$ Ionophore VI
Bis[(12-crown-4)methyl] dodecylmethylmalonate

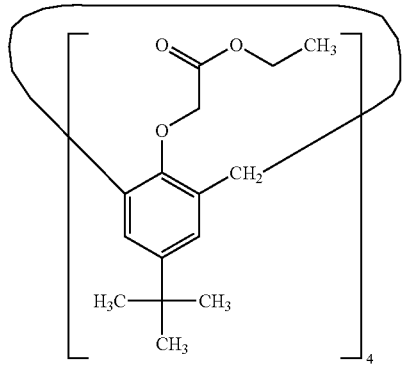

Na$^+$ Ionophore X
4-tert-Butylcalix[4]arene-tetraacetic acid
tetraethylester

-continued
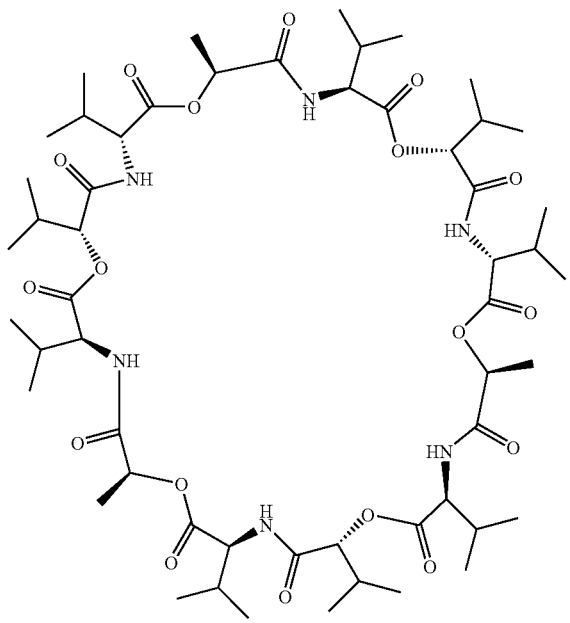
K+ Ionophore I
Valinomycin
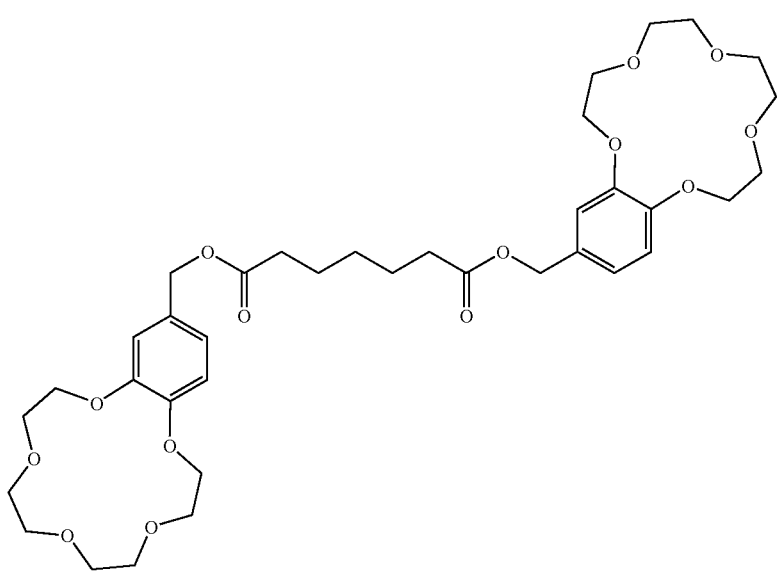
K+ Ionophore II
Bis[(benzo-15-crown-4)-4'-ylmethyl]pimelate

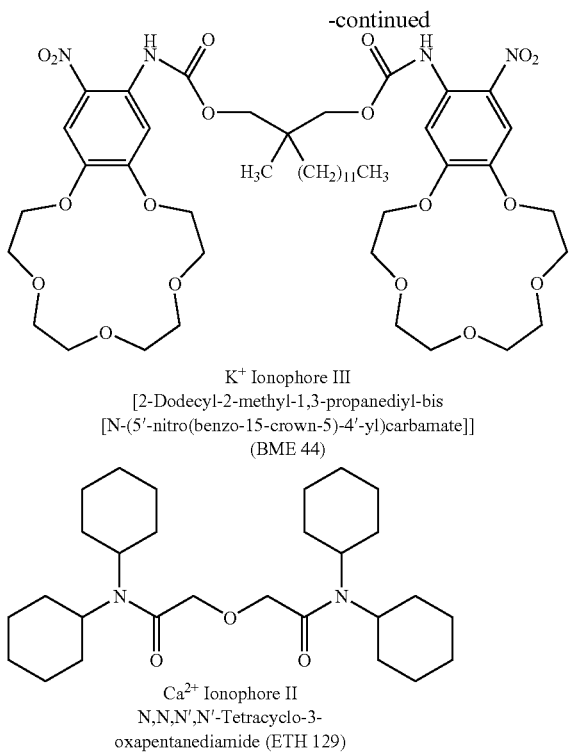

K⁺ Ionophore III
[2-Dodecyl-2-methyl-1,3-propanediyl-bis
[N-(5'-nitro(benzo-15-crown-5)-4'-yl)carbamate]]
(BME 44)

Ca²⁺ Ionophore II
N,N,N',N'-Tetracyclo-3-
oxapentanediamide (ETH 129)

The selectivity of ionophores for their given ions can be measured using various methods. Two such methods, the Fixed Interferent Method and the Matched Potential Method are described below.

The Fixed Interferent Method:

In this method selectivity coefficients are analysed according to the Nicolsky-Eisenman equation:

$$E_m^{0'} = E_i^{0'} + s \log[c_i + K_{ij} c_j^{z_i/z_j}]$$

Where $E_m^{0'}$ is the mid point potential of the redox process, $c_i$ is the concentration of ion i and $c_j$ is the concentration of ion j, $Z_i$ and $Z_j$ are the charges of ion i (primary ion) and ion j(interfering ion) respectively, s signifies the selectivity (2.303 RT/nF) and $K_{ij}$ is the selectivity coefficient.

If K is larger than 1, the ISE responds to the interfering ions more selectively than to the primary ions. If K is smaller than 1, the ISE responds to the primary ions more selectively than to interfering ions. The Nicolsky-Eisenman equation assumes a Nernstian response not only for the primary ion but also for the interfering ion.

Figure 5:
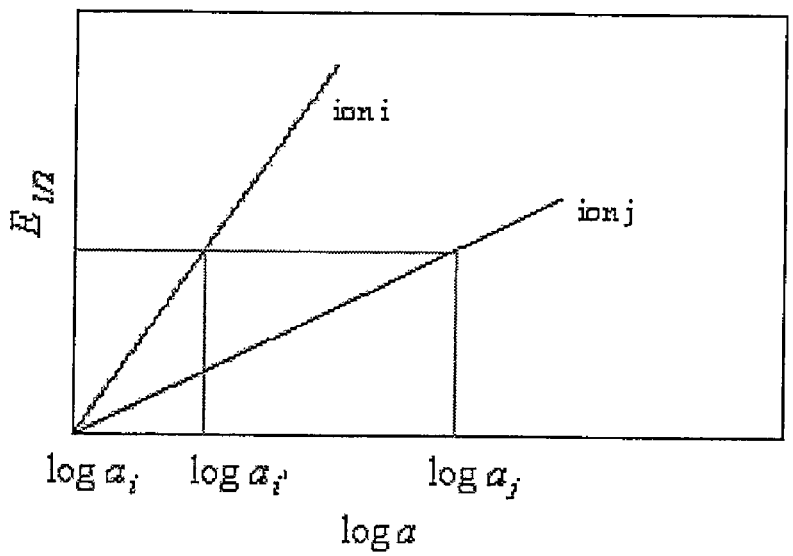
FIG. 5 demonstrates the matched potential method for determining an ISE selectivity coefficient.

Matched Potential Method (MPM):

The MPM involves, in a first step, measuring the increase in potential with increasing concentration of a primary analyte ($a_i$). Then, in a second step, holding the primary analyte ($a_i$) concentration constant while increasing the interfering ion concentration ($a_j$) until a similar shift in potential of the system is observed as is obtained on addition of the primary analyte in the first step. This is depicted in FIG. 5, wherein $\Delta a = a_{i'} - a_i$, where $a_i$=initial primary analyte concentration; $a_{i'}$=primary analyte concentration after potential shift; $a_j$=change in interfering ion concentration. The MPM can not be directly related to Nicolsky-Eisenman selectivity coefficients, but it does allow a selectivity to be determined with different charged ions, and is easier to calculate than fixed interference or separate solution methods. The selectivity coefficient $k_{i,j}^{MPM}$ is then determined by $$k_{i,j}^{MPM} = \Delta a_i / a_j \quad\quad 1$$

Figure 6:
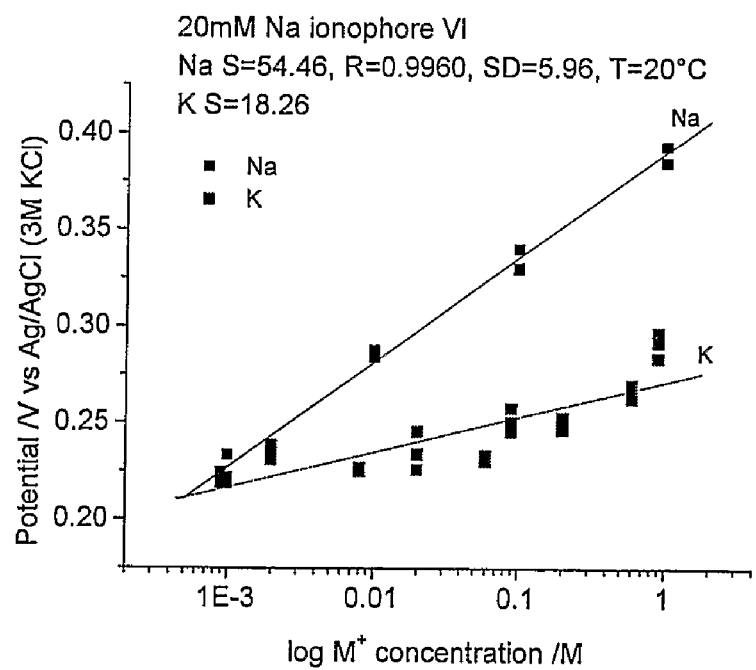
FIG. 6 shows the selectivity of a thin film, measured according to the Matched Potential Method, with 20 mM Na ionophore VI at a scan rate of 100 mV s$^{-1}$ adding KCl with a constant background of 1 mM Na. S=the gradient (slope) of the graph, R=correlation coefficient, SD=standard deviation and T=temperature.

An example of the MPM method for determining selectivity of a thin film with Na ionophore VI is shown in FIG. 6 using the sensor described in Example 5(a) (primary analyte, i=Na⁺, upperline; interfering ion, j=K⁺, lower line). Approximately a 54 mV shift in response is seen when changing the Na⁺ concentration from 0.65 mM ($a_i$) to 6.5 mM ($a_{i'}$) ($\Delta a$=5.85) and a corresponding 54 mV shift is induced by changing the K⁺ concentration from 1 mM to 920 mM in the presence of 1 mM Na⁺ ($a_j$=919). Thus $k_{Na^+,K^+}^{MPM}$=5.85/919=6.36E–3 and log $k_{Na^+,K^+}^{MPM}$=–2.19 which is very similar to other published results and is sufficient for the determination of Na⁺ in blood.

In a preferred embodiment of the invention, the support matrix also contains a solvent in which the electroactive species and ionophore can be at least partially dissolved. The solvent may be an inert organic solvent. Alternatively, the solvent may be a plasticizer which acts not only to dissolve the electroactive species and ionophore, but also to ensure that the support matrix is not brittle. The plasticizer may be any material which provides these properties and many examples are commercially available. Suitable materials for use as the plasticizer include bis(1-butylpentyl)decane-1,10-diyl diglutarate (ETH469), 2-nitrophenyl octyl ether (NPOE), bis(2-ethylhexyl) sebacate and bis(1-butylpentyl) adipate.

In an alternative embodiment of the invention, an ionic liquid is used as a solvent. Ionic liquids have a negligible vapour pressure, low toxicity, high chemical, electrochemical and thermal stability, high conductivity and the ability to dissolve a wide range of organic and inorganic compounds. Each of these properties provides corresponding benefits to the devices of the invention. In particular, the high conductivity of the ionic liquid is of benefit as it increases the conductivity of the membrane. Ionic liquids may also have a low solubility in aqueous liquids and therefore will remain in the support matrix rather than leaking into the fluid, which is typically aqueous.

Examples of ionic liquids which can be used as solvents include 1-ethyl-3-methylimidazolium bis(trifluoromethane sulfonyl)amide (emim.tfsa), N-butyl-bis(trifluoromethane-sulfonyl)amide (P14.tfsa) and trihexyl(tetradecyl)-phosphonium tris(pentafluoroethyl)trifluorophosphate (aph4.cph12). Further examples include tri-hexyl-tetradecyl-phosphonium bis(2,4,4-trimethyl-pentyl)phosphinate; 1-ethyl-3-methyl-imidazolium bis(pentafluoroethylsulfonyl)imide; 1-butyl-1-methyl-pyrrolidinium bis(trifluoromethylsulfhonyl)imide; 1,2-dimethyl-3-propyl-imidazolium bis(trifluoromethylsulfhonyl)imide; 1-ethyl-3-methyl-imidazolium bis(trifluoromethylsulfhonyl)imide; 3-methyl-1-propyl-pyridinium bis(trifluoromethylsulfhonyl)imide; methyl-trioctyl-ammonium bis(trifluoromethylsulfhonyl)imide; trihexyl-tetradecyl-phosphonium bis(trifluoromethylsulfhonyl)imide; trihexyl-tetradecyl-phosphonium chloride; trihexyl-tetradecyl-phosphonium decanoate; trihexyl-tetradecyl-phosphonium dicyanamide; 1-butyl-3-methyl-imidazolium hexafluorophosphate; 1-hexyl-3-methyl-imidazolium hexafluorophosphate; 1-methyl-3-octyl-imidazolium hexafluorophosphate-tetrabutyl-ammonium; heptadecafluoro-octance sulfonate; and trioctylmethylammonium thiosalicylate.

It is preferred that the support matrix phase of the present invention has a high conductivity. Where an ionic liquid is used as a solvent, the conductivity is typically inherently high. However, where other solvents, e.g. plasticizers are used or where a solvent is absent, it is preferred that the support matrix contains an ionic salt in order to increase the conductivity. Preferred ionic salts have a high solubility in any solvent that is used in the support matrix phase, but are substantially insoluble in the fluid (typically they are substantially insoluble in water). This helps to keep the ionic salt in the support matrix phase.

The ionic salt is also typically electro-inactive at the potentials used for the sensing measurement.

For a cation selective electrode, application of a potential to the electrode will cause a build up of negative charge in the support matrix. The charge is neutralized by ingress/egress of the cation to be detected from aqueous solution into the support matrix. In order to ensure that cations move from the fluid into the support matrix, it is important to ensure that the charge is not neutralised by other means, for example by the anion of the ionic salt moving out of the support matrix and into the fluid. Therefore, the process of the anion of the ionic salt moving into the fluid should be less favourable than the process of the cation to be detected moving into the support matrix. Typically, this is achieved by using a large anion for the ionic salt. Similarly, for an anion sensor, the cation of the ionic salt is typically a large ion to ensure that the process of the cation moving into the fluid is less favourable than that of the anion to be detected moving into the support matrix. Typically, an ionic salt having a large cation and anion component is used such that the diffusion of both ions out of the support matrix is low.

A large number of different ionic salts can be employed in the present invention and the skilled person would be able to select suitable salts based on the above description. Examples of suitable ionic salts having a large cation component include tetra alkyl, for example tetra($C_4$-$C_{16}$ alkyl) ammonium salts, e.g. tetra($C_4$-$C_8$ alkyl) ammonium salts. Examples of suitable ionic salts having a large anion component include tetra($C_4$-$C_{16}$ alkyl) or tetraphenyl borates, carboranes and perchlorate, for example tetra($C_4$-$C_8$ alkyl) or tetraphenyl borates and perchlorate. Particular examples of ionic salts include tetrabutylammonium tetraphenylborate (TBATPB), tetrahexylammonium perchlorate (THAClO$_4$) and tetraheptylammonium perchlorate (THAClO$_4$) (e.g. TBATPB and tetrahexylammonium perchlorate). Tetrahexyl and tetraheptylammonium borate and tetraphenylborate can also be used.

The sensing electrodes can be produced by a drop coating method. The electrically conducting support is optionally prepared, for example by polishing and/or cleaning. A coating solution is then introduced on the surface of the support and dried. Drying is typically carried out by air drying, for example for up to 10 minutes.

The coating solution comprises the support matrix material, electroactive species, ionophore and any other reagents used dissolved in a suitable solvent, for example THF. Typically, the ionophore (concentration from 5 to 50, preferably 20 to 30 mmol dm$^{-3}$), electroactive species (concentration from 0.5 to 5, preferably 2 to 3 mmol dm$^{-3}$) and optional ionic salt (concentration up to 50 mmol dm$^{-3}$) are first dissolved in the plasticizer or ionic liquid (or other solvent if appropriate). The plasticizer or ionic liquid (or other solvent if appropriate) is then combined with a solution of the support matrix. Typically, the ratio of support matrix solution: plasticizer or ionic liquid is from 100:1 to 50:1.

Whilst in the embodiments described herein, an ionic salt is incorporated into the support matrix by the drop coating method, i.e. by dissolution of the ionic salt in a solvent which is subsequently placed onto the electrode surface and the solvent allowed to evaporate, the skilled person will be aware of other methods of using ionic salts to form the support matrix.

The devices of the invention comprise at least one sensing electrode as described above together with one or more further electrodes. Typically, the device comprises a counter electrode to which a potential is applied and a reference electrode which provides a potential reference (i.e. a 3-electrode system), although the counter and reference electrodes may be combined (i.e. a 2-electrode system) and provided as a single pseudo reference electrode if desired. A suitable reference compound, such as a ruthenium compound, e.g. ruthenium hexamine chloride, may also be used. The device of the invention may comprise more than one sensing electrode.

In a preferred embodiment, all of the electrodes are formed on a single base, for example by printing two (or more as desired) conducting tracks onto an insulating base using a conductive ink. A support matrix is deposited on the sensing electrode as described above. In a preferred embodiment, the sensing electrode is a carbon electrode, the counter electrode is a metal for example platinum, whilst the reference (or pseudo reference) electrode is formed of silver/silver chloride.

The method of the invention is carried out by contacting the fluid to be tested with the sensing electrode as well as the counter and reference (or pseudo reference) electrode(s). A time varying potential is then applied to the sensing electrode and the current measured during application of the potential. The potential at which the current peaks is determined. Typically, the potential is scanned, for example by first decreasing the applied potential from a determined maximum to substantially zero and optionally increasing the applied potential, e.g. to said determined maximum. Alternatively, the scan may include first increasing the applied potential from substantially zero to a determined maximum, and then reducing the applied potential to substantially zero. A typical voltammogram determined using such a method is depicted in FIG. 1. This measurement was carried out on the $K^+$ voltammetric sensor described in Example 2. The current peak can be observed at approximately 0.5V for oxidation and 0.45V for reduction. The average of more than one scan may be used.

The scan is typically applied as described above with reference to a silver/silver chloride reference. However, alternative references may used, including a $Ru(NH_3)_6Cl_3$ reference. The skilled person would be able to determine a suitable reference to use which is insensitive to the concentration of the ion under test. Thus, for example, a silver/silver chloride reference should be avoided when measuring chloride concentration and a $Ru(NH_3)_6Cl_3$ reference may be used instead. The scan may also be carried out around a potential other than zero. For example, the potential may be decreased from a determined maximum to a determined minimum (which may or may not be zero) and then subsequently increased again to the determined maximum.

The maximum potential for the potential scan will depend on the electroactive substance used, as well as other factors such as the ion to be detected. The maximum potential should, in any case, be above the potential at which the peak in the current is observed. The skilled person would be able to determine suitable potential scan ranges to apply in each individual case by carrying out a trial voltage scan and determining the approximate level at which the current peaks.

The scan rate is typically from $0.005\ Vs^{-1}$ to $5\ Vs^{-1}$, preferably from $0.01\ Vs^{-1}$ to $1\ Vs^{-1}$.

In a preferred embodiment of the invention, the electroactive substance is reversibly oxidised and reduced. In this case, carrying out a potential scan leads to two current peaks: an oxidation peak and a reduction peak. This is depicted in FIG. 1 where peaks are observed at 0.5V and 0.45V. In this embodiment, a more accurate measurement can be obtained by averaging the potentials at which the peaks occur. This embodiment also has the advantage that the potential can be applied before the system has reached a true equilibrium since averaging the two potentials in this manner reduces the error in the measurement which is seen as a result of a non-equilibrium system.

The method of the present invention can be carried out on a wide variety of fluids, although aqueous liquids are preferred. Preferred fluids have a concentration of the ion to be detected (for example $K^+$, $Na^+$, $Ca^{2+}$ or $Cl^-$, e.g. $K^+$, $Na^+$ or $Cl^-$) of from $0.1\ \mu mol\ dm^{-3}$ to $1.0\ mol\ dm^{-3}$. More preferably, fluids have a concentration of the ion to be detected (for example $K^+$, $Na^+$, $Ca^{2+}$ or $Cl^-$, e.g. $K^+$, $Na^+$ or $Cl^-$) of from $0.1\ mmol\ dm^{-3}$ to $1.0\ mol\ dm^{-3}$. Examples of fluids which can be tested include body samples such as blood, urine and saliva, environmental liquids or drinks, e.g. body samples. The method of the invention is particularly useful in the quantitative determination of $K^+$, $Na^+$ $Ca^{2+}$ and $Cl^-$ (e.g. $K^+$, $Na^+$ and $Cl^-$) in the blood, since the selectivity relative to other blood components is very high. Alternative uses of the invention include the quantitative detection of anions or cations in water samples such as sea water or drinking water, and in beverages and food stuffs.

EXAMPLES

Example 1

Production of Device

A conventional three-electrode cell was employed, with 1.5 mm diameter glassy carbon (GC) electrode as the sensing electrode, and a Pt wire as the counter electrode. A Ag/AgCl (3 M NaCl) electrode was used to provide the reference potential scale. The GC sensing electrode was polished with a 0.3 μm $Al_2O_3$ (Buehler) slurry, washed successively with water and acetone and dried with tissue paper.

A coating composition was then prepared by combining 1 ml PVC solution (0.15 g PVC dissolved in 8 ml THF), with 37.5 μl NPOE (plasticizer) which contains 2.5 mM TCNQ (electroactive species), 25 mM valinomycin (ionophore) and 10 mM TBATPB (ionic salt). A small volume (less than 1 μl) of coating solution was introduced on to the surface of the glassy carbon (GC) electrode using a micropipette. The sensor was then left in the air for about 5 minutes to allow the THF to evaporate.

Example 2

$K^+$ Sensor

A measurement was carried out using a $0.1\ mol\ dm^{-3}$ solution of KCl as the fluid. The fluid was contacted with the electrodes of a device produced in accordance with Example 1 and a potential scan was applied to the sensing electrode, the scan involving increasing the applied potential from substantially zero to 0.8V and then reducing the applied potential to zero again. The current was measured during application of the scan. A voltammogram showing the results is depicted in FIG. 1. Scan rates of between $10\ mVs^{-1}$ and $1\ Vs^{-1}$ were used and the measurement was found to be independent of the scan rate within this range.

Figure 2:
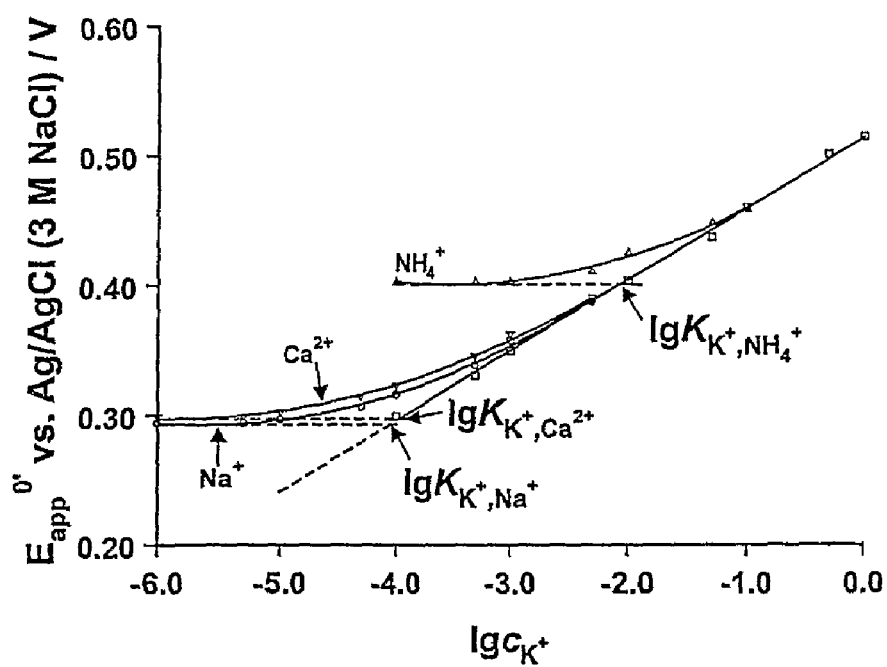
FIG. 2 depicts the measurement of selectivity coefficients for a $K^+$ sensor according to the invention, in the presence of $Na^+$, $NH_4^+$ and $Ca^{2+}$.

The selectivity of this sensor was determined in relation to $Na^+$, $NH_4^+$ and $Ca^{2+}$ ions using the fixed interference method recommended by IUPAC (Morf: The Principles of Ion Selective Electrodes and of Membrane Transport, Elsevier: Amsterdam, 1981). The concentration of interference ion was fixed at $1.0\ mol\ dm^{-3}$ and the concentration of target ion ($K^+$) was varied from $10^{-3}\ mmol\ dm^{-3}$ to $0.1\ mol\ dm^{-3}$. The results of this experiment are depicted in FIG. 2. In this Figure, the working curve of the $K^+$ sensor is obtained using different concentrations of KCl in the absence of interference ion. The other three curves are obtained at varying KCl concentrations in the presence of $1.0\ mol\ dm^{-3}\ Na^+$ (O), $NH_4^+$ (Δ) or $Ca^{2+}$ (∇). The resulting values of lgK in the presence of $Na^+$, $NH_4^+$ and $Ca^{2+}$ are, respectively, −4.05, −2.07 and −3.97.

Example 3

Alternative $K^+$ Sensor

Figure 3:
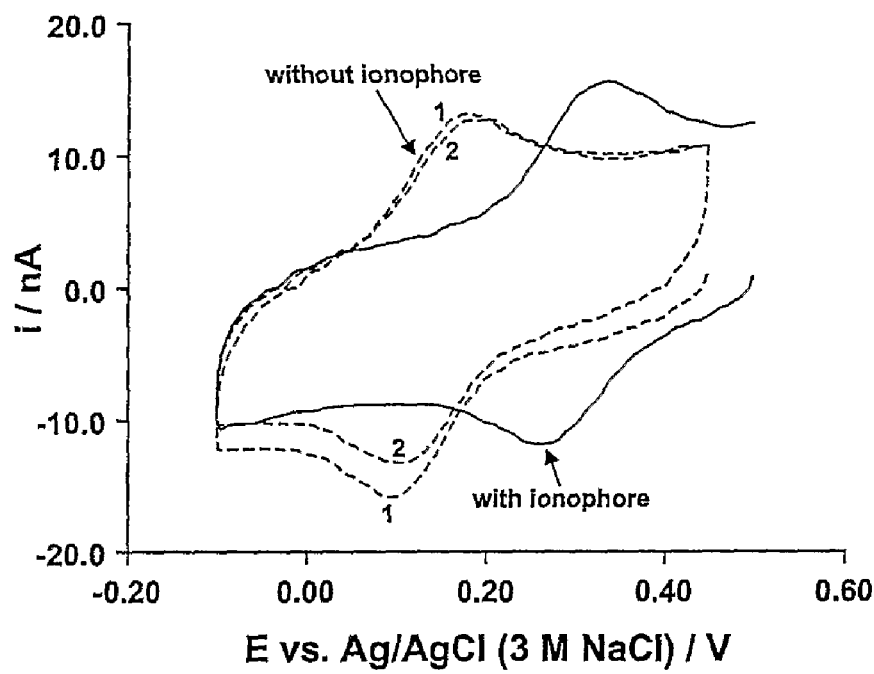
FIG. 3 depicts a voltammogram obtained using a $K^+$ sensor according to an alternative embodiment of the invention.

A sensor was produced in the same manner as described in Example 1, but replacing the NPOE plasticizer with the ionic liquid aph4.cph12 and eliminating the ionic salt (TBATPB). A measurement was carried out using a $0.1\ mol\ dm^{-3}$ solution of KCl as the fluid in the same manner as is described in Example 2. The resulting voltammogram is depicted in FIG. 3. The solid line indicates the result for the above described sensor, whilst the dotted lines depict the result for a sensor which varied from the above only in that an ionophore was not used. In the absence of ionophore, the transfer of $K^+$ into the membrane is less favourable resulting in movement of the oxidation and reduction peaks and decreasing peak current with cycle number due to redox active species transferring into the aqueous phase.

Example 4

Na+ Sensor

Figure 4:
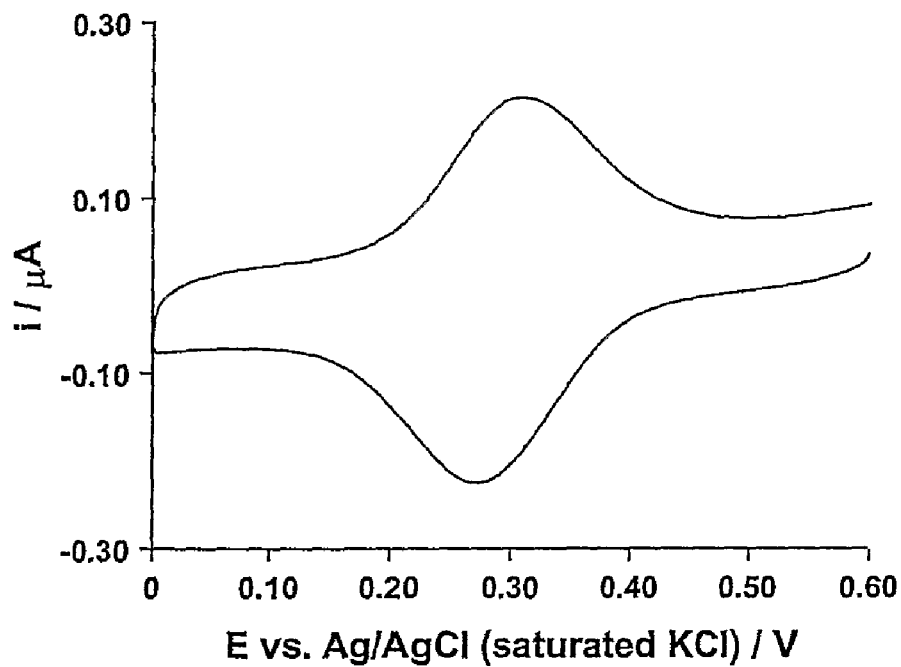
FIG. 4 depicts a voltammogram obtained using a $Na^+$ sensor according to one embodiment of the invention.

A sensor was produced in the same manner as described in Example 1, but replacing the valomycin ionophore with 25 mmol dm$^{-3}$ bis[12-crown-4)methyl]dodecylmethylmalonate. A measurement was carried out using a 0.1 mol dm$^{-3}$ solution of NaCl as the fluid in the same manner as is described in Example 2. The resulting voltammogram is depicted in FIG. 4.

Example 5

Alternative Embodiment of the Voltammetric ISE (VISE)

Voltammetric experiments were performed with an Autolab PGSTAT100 (ECO-Chemie) electrochemical workstation or a home built potentiostat controlled by LabVIEW with automatic peak detection software using a standard 4-necked electrochemical cell. A 3 mm diameter glassy carbon (GC) (IJ Cambria) was used as the working electrode, polished with a 0.3 μm alumina slurry on Microcloth polishing cloth, rinsed in deionised water and dried prior to use. The Ag/AgCl (aqueous 3 M KCl) reference electrode had an internal filling solution of 3 M NaCl when testing the K$^+$ and Ca$^{2+}$ ion-sensors and 3 M KCl when testing all other ion-sensors to prevent contamination of testing solutions with the internal filling solution. The auxiliary electrode was made from platinum mesh.

The thin film was prepared by dissolving 50 mg of PVC into 4 mL THF, 1 mg of TCNQ into 2 mL THF and 2.6 mg of tetrahexylammonium tetraphenylborate (THATPB) into 1 mL THF. 1 mL of PVC solution (or 50 mg of dielectric ink) was then combined with 100 mL of THATPB solution, 40 μL of TCNQ solution, 37.5 μL of NPOE (nitrophenyl octyl ether) and ionophore. 1 μL was then placed onto the electrode surface and the THF allowed to evaporate giving a PVC supported NPOE membrane containing 10 mM THATPB, 2.5 mM TCNQ and 20 mM ionophore. Electrodes were produced using (a) Na ionophore VI, (b) K ionophore III and (c) Ca ionophore II.

During testing of the various ion-sensors, the film was contacted with an appropriate fluid sample and a time varying potential applied. The initial applied potential was 0.8V and this was reduced to zero and increased to 0.8V again. The current was recorded during application of the potential and typically the Em (midpoint potential) determined. All thin film measurements were taken in the first potential cycle at a scan rate of 100 mV s$^{-1}$ with a film thickness of 1 μL. These conditions were applied for all of Examples 6 to 10, except where otherwise indicated.

Example 6

Alternative Na+ Sensor

Figure 7:
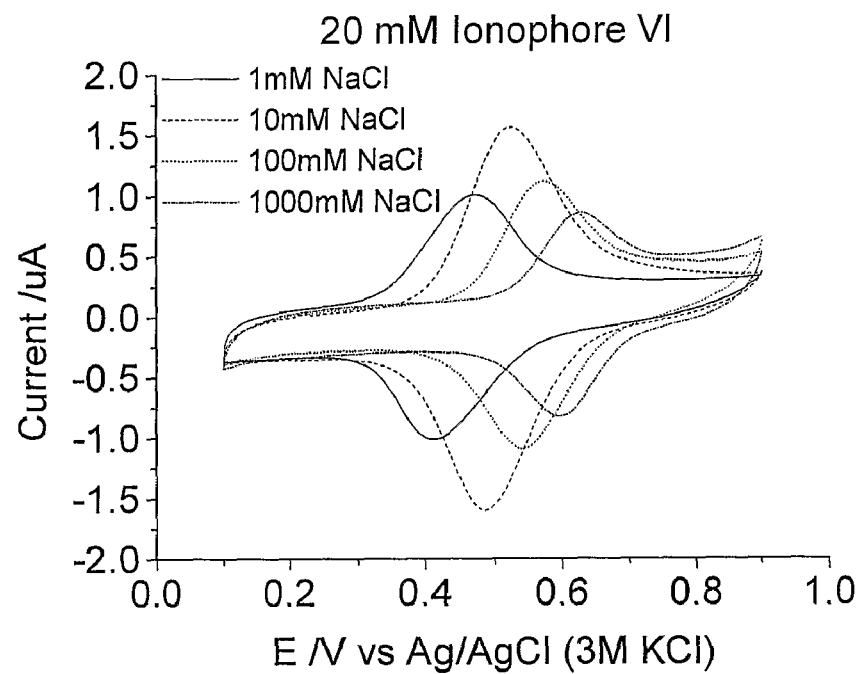
FIG. 7 depicts the results of cyclic voltammetry using the sensor of Example 6.
Figure 7:
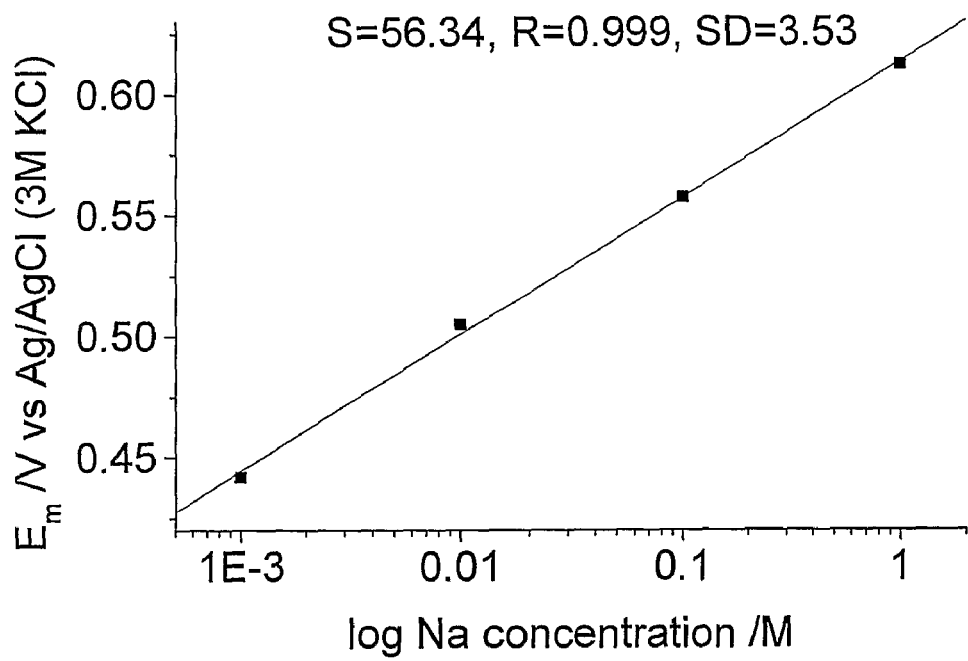

Cyclic voltammetry was conducted on a thin film containing 2.5 mM TCNQ, 10 mM THATPB and 20 mM Na ionophore VI. All other aspects were as described above in Example 5. The film was contacted with several aqueous solutions containing varying concentrations of Na$^+$ ions and the potential scan of Example 5 applied. Variation of the Na$^+_{(aq)}$ concentration from 1 to 1000 mM shifted the $E_m$ of reaction (FIG. 7*a*). In order to reduce error which might occur on replacing the thin film, the same film was used to carry out the measurements on each solution. Thus, testing was started with a 1 mM NaCl solution; the film was then rinsed with distilled water and used again for a 10 mM NaCl solution and so on. Due to the repeated use of the one film, a small amount of TCNQ transferred into the aqueous phase giving smaller peak heights on subsequent samples. The thin film sensor has very small currents and therefore is not affected from IR$_u$ (IR drop, i.e. the current times the uncompensated resistance) down to 1 mM Na$^+$. A plot of the $E_m$ versus log Na$^+$ concentration (FIG. 7(*b*)) shows a linear response with a slope of 56.34 mV per decade.

Example 7

Sensor Using Ru(NH$_3$)$_6$Cl$_3$ as a Reference Compound

Figure 8:
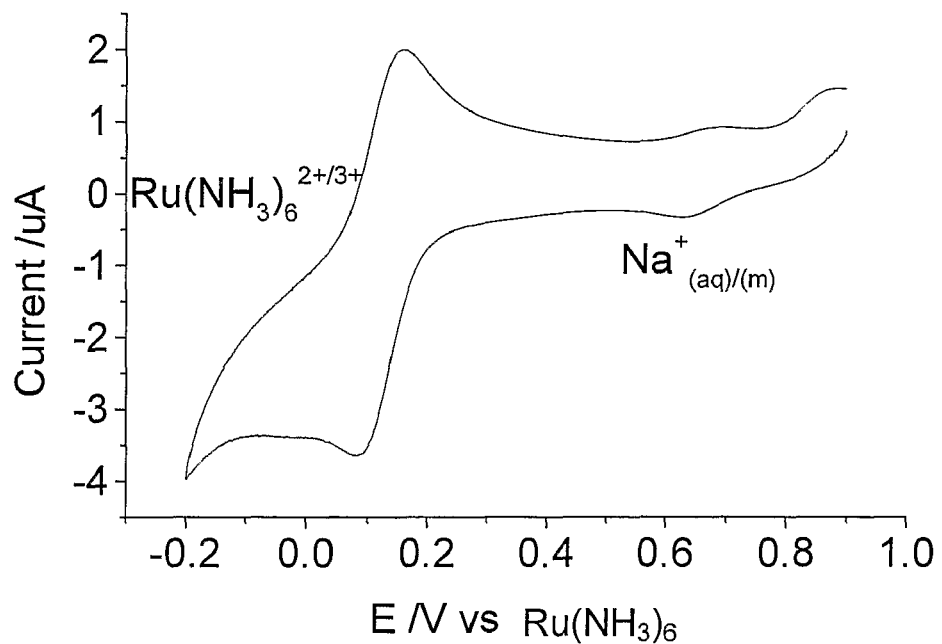
FIG. 8 depicts the results of Example 7 involving calibration of a thin film with 10 mM Na ionophore VI in 1000 mM NaCl at a scan rate of 100 mV s$^{-1}$ versus Ru(NH$_3$)$_6$Cl$_3$.

The determination of ion concentration by voltammetry and measuring peak position allows the use of an internal standard such as Ru(NH$_3$)$_6$Cl$_3$. It is common to have an electrode system that uses the Ag/AgCl counter electrode as a pseudo reference electrode. Ideally, the reference system should be insensitive to the ion under test. Hence when measuring chloride it is preferable not to use Ag/AgCl as it is affected by the Cl− concentration in the fluid under measurement (e.g.blood). An example of a redox couple which can be used to overcome this problem is Ru (NH$_3$)$_6$Cl$_3$ which is inert with respect to chloride ion concentration in the fluid and can be used to calibrate the electrode system. In order to do this a VISE was produced according to the methods of Example 5. Since, in the thin film VISE, the film coats the electrode, preventing penetration of Ru(NH$_3$)$_6$Cl$_3$ to the electrode surface, a small hole was scratched into the film exposing the electrode before placing it into the solution. The scan rate was as described in Example 5. A response was then obtained for both the VISE and Ru(NH$_3$)$_6$Cl$_3$ allowing the VISE $E_m$ to be referenced to the Ru(NH$_3$)$_6$Cl$_3$ $E_m$ (FIG. 8). This is a possible method of VISE calibration, however placing a hole in the membrane may not be reproducible and could affect the sensitivity or selectivity of the film. It also possible that a separate working electrode be used for the determination of the Ru(NH$_3$)$_6$Cl$_3$ $E_m$ to calibrate the VISE.

Example 8

Application of VISE to Sea Water and Drink Samples

To ensure the thin film VISE can be used on complex samples, sea water and Gatorade were obtained to determine their Na$^+$ and K$^+$ concentrations. The Na and K ion sensors of Example 5 were used. The values obtained were compared to the label on the drink bottles and to the results obtained using a commercial potentiometric membrane ISE (Metrohm) (Table 1). The ISEs were first calibrated by creating a concentration versus $E_m$ plot using solutions of known Na or K ion concentration, and the $E_m$ values of the complex samples then measured and used to calculate the analyte concentration.

The Na$^+$ VISE gave a Na$^+$ concentration of 21 mM for the Gatorade, which is in good agreement with the commercial sensor and the concentration claimed on the bottle. The sea water had a Na$^+$ concentration of 298 mM as determined by the VISE, but the potentiometric ISE gave a concentration of 480 mM (measurement after 1-2 minutes and without adjusting for drift due to stabilization time). However, due to the potentiometric sensor requiring an equilibrium, the sea water measurement required 5 minutes to stabilize as opposed to 1-2 minutes for the other solutions. The drift over the extra 3-4 minutes whilst stabilization occurred was 10 mV. When this amount is subtracted from the measured potential to obtain a more accurate result, a Na$^+$ concentration of ~300 mM is obtained, which is in good agreement with typical sea water Na$^+$ concentrations. The time required for the potentiometric membrane ISE to reach equilibrium and the errors associated with it indicate that the VISE can obtain more accurate results more rapidly.

The K$^+$ VISE determined the sea water K concentration to be 8.9 mM, in excellent agreement with the Metrohm ISE and typical sea water K$^+$ concentration. The Gatorade had a K$^+$ concentration of 21 mM, also in good agreement with the Metrohm ISE and the claimed K$^+$ concentration.

TABLE 1

Comparison of VISE, Metrohm ISE and claimed concentrations of Na$^+$ and K$^+$ in sea water and Gatorade.

| | Na$^+$/mM | | | K$^+$/mM | | |
|---|---|---|---|---|---|---|
| | Claimed | VISE | Metrohm ISE | Claimed | VISE | Metrohm ISE |
| Sea Water | ~400 | 298 | 300 | ~10 | 8.9 | 9.0 |
| Gatorade | 21 | 21 | 23 | 6 | 6.7 | 8.8 |

Example 9

Sensor Using Dielectric Ink to Form the Support Matrix

Two electrodes were produced in the same manner as Example 5 but using 12.5 mg of dielectric ink combined with NPOE, TCNQ (dissolved in THF), THATPB (dissolved in THF) and 20 mM ionophore to form the thin film. Na ionophore VI was used as the ionophore in one electrode and K ionophore III was used as the ionophore in the second. 0.2 µl of this solution was drop cast onto a glassy carbon working electrode and THF allowed to evaporate giving a dielectric ink/NPOE support matrix containing TCNQ, THATPB and ionophore.

Figure 9:
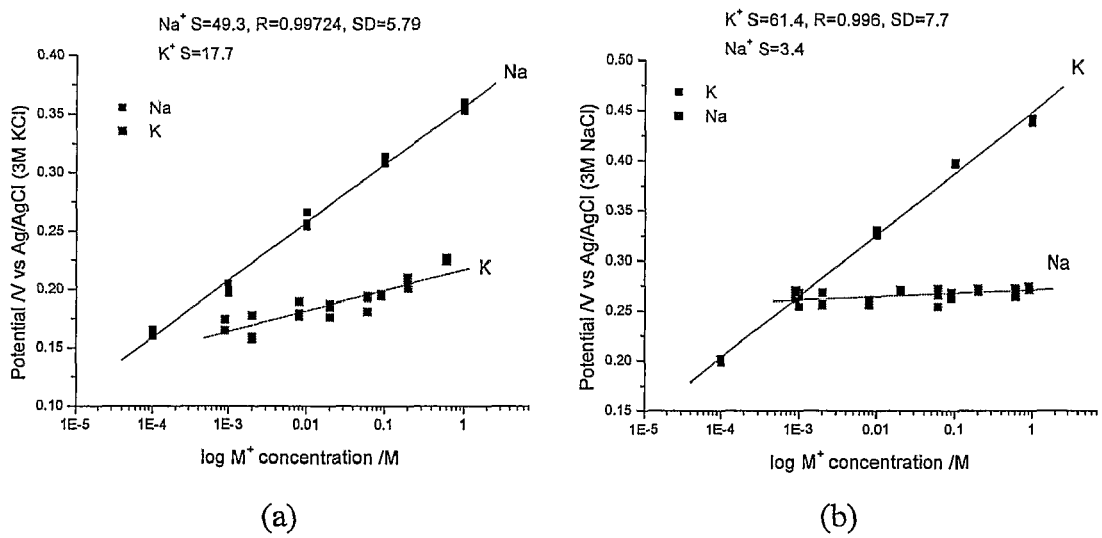
FIG. 9 depicts the results of Example 9 involving cyclic voltammetry of a 0.2 μl dielectric ink supported thin film at a scan rate of 100 mV s$^{-1}$ (a) sensitivity and selectivity of Na ionophore VI, measured according to the Matched Potential Method, in the presence of aqueous solution of Na$^+$ (b) sensitivity and selectivity of K ionophore III in the presence of aqueous solution of K$^+$. S=the gradient (slope) of the graph, R=correlation coefficient and SD=standard deviation. The comparison between the slopes for Na$^+$ and K$^+$ help indicate selectivity. For example in FIG. 9b, a change in Na$^+$ concentration has very little effect on the potential, whereas changes in K$^+$ concentration can be correlated to a significant change in potential, showing that K$^+$ ionophore III is selective for K$^+$ over Na$^+$.

Cyclic voltammetry according to the Matched Potential Method was carried out on both electrodes in aqueous solutions having varying concentrations of (a) Na$^+$ for Na ionophore and (b) K$^+$ for K ionophore. The results are shown in FIG. 9.

As shown in FIG. 9(a), the sensitivity of the dielectric ink supported VISE with 20 mM Na ionophore VI was the same as the PVC supported VISE of Example 5 being 49.3 mV per decade. The selectivity over K$^+$ was slightly higher than the PVC supported VISE with log $k_{NA^+,K^+}^{MPM} = -2.71$.

As shown in FIG. 9(b), the sensitivity of the dielectric ink supported VISE with 20 mM K ionophore III was also similar to the PVC supported VISE being 61.4 mV per decade. The selectivity over Na$^+$ was log $k_{K^+,Na^+}^{MPM} = -3.39$.

Example 10

Application of VISE to Measure Ca$^{2+}$ in Whole Blood and Plasma

Readings from an AEROSET 2 lab analyzer were used in order to gauge the accuracy of the results obtained using the Ca$^{2+}$ VISE of the invention. The AEROSET 2 performs most chemical analyses by spectrophotometric techniques—the exceptions being sodium and potassium, which are carried out by ISE. The AEROSET 2 determines the sodium and potassium activity directly, but for calcium it measures total calcium rather than free calcium. A formula (given below) is typically used to determine the free calcium from the total calcium concentration and the albumin concentration.

Free Calcium (mM)=Total Calcium (mM)+0.02(40−Albumin (g/L))

Typical ranges for sodium, potassium, calcium and chloride activities are listed for blood plasma (Table 2). There are several factors that can affect the response of an ISE in plasma. Hemodilution by more than 20% affects ionic strength of the plasma and a suitable ionic solution should be used. The addition of sodium heparin will increase the concentration of sodium in the sample. Heparinized plasma will cause the potassium concentration to drop initially and then rise. Freezing or blood coagulation will cause the potassium concentration to rise. Free calcium levels will also drop after prolonged tourniquet application and exercise (due to binding by lactate), exposure to air (complexation with $CO_2$), heparin exposure (1 IU of heparin will decrease calcium activity by 0.01 mM) and freezing.

TABLE 2

Normal ranges for plasma sodium, potassium, calcium and chloride.

| | Ion activity range/mM |
|---|---|
| Na | 137-145 ± 1 mM |
| K | 3.5-4.9 ± 0.1 mM |
| Ca | 1.12-1.32 mM |
| Cl | 98-109 ± 1 mM |

Figure 10:
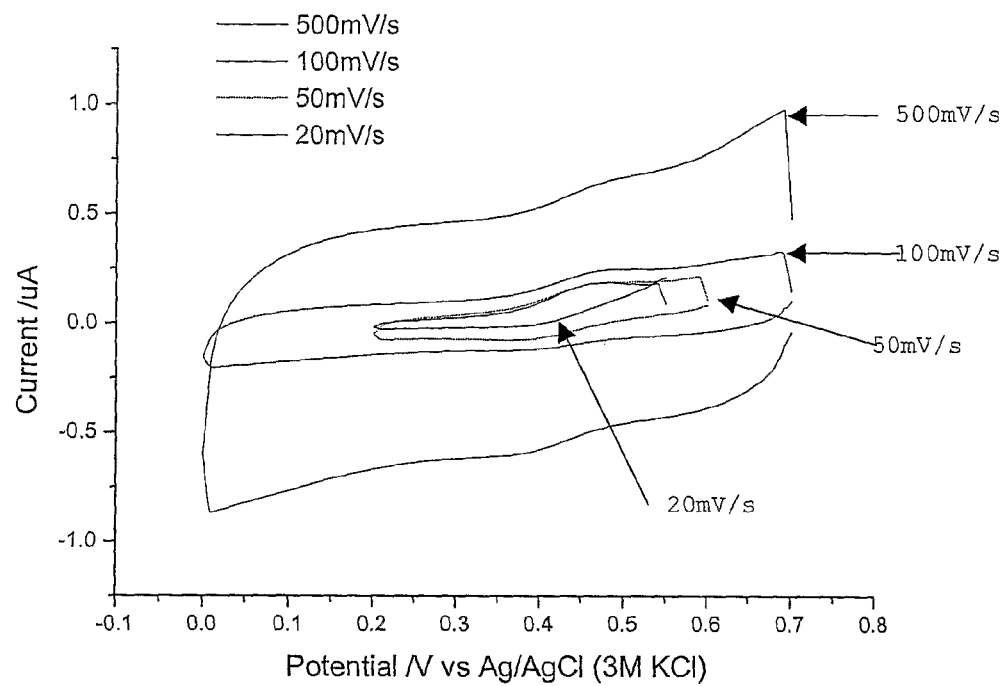
FIG. 10 depicts the results of Example 10 involving cyclic voltammetry of a thin film voltammetric ISE with 20 mM Ca ionophore II in plasma with (a) scan rates of 20 mVs$^{-1}$, 50 mVs$^{-1}$, 100 mVs$^{-1}$ and 500 mVs$^{-1}$ with a 1 μl thin film (b) 1 μl, 2 μl and 4 μl thin film thicknesses at a scan rate of 100 mV s$^{-1}$.
Figure 10:
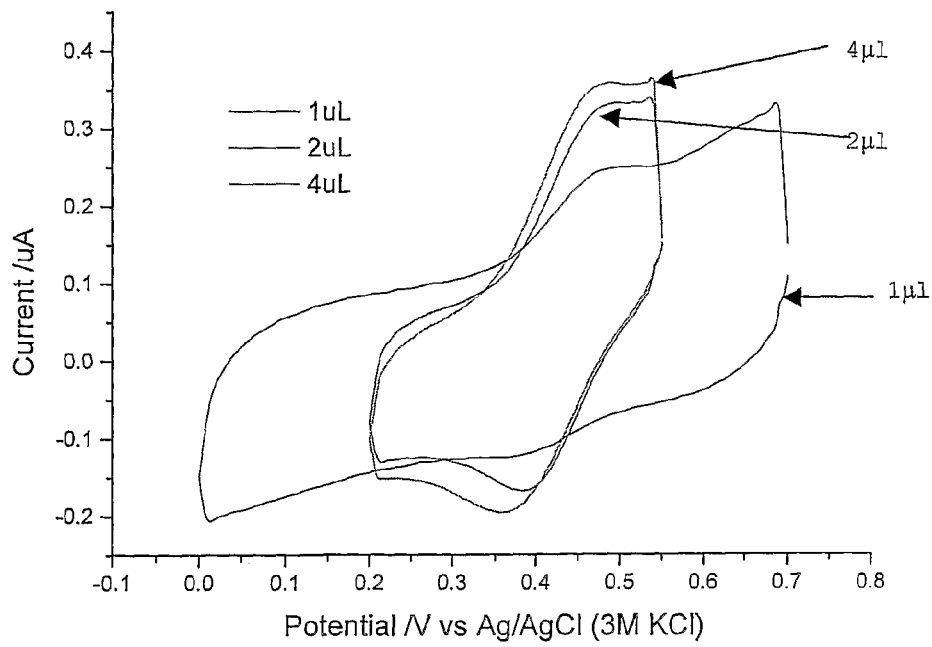

Nine plasma samples were collected for sodium, potassium and calcium determination. Two of those samples were also tested as whole blood and another two were frozen and thawed. Ca$^{2+}$ concentrations were measured using the Ca VISE described in Example 5. The VISE was initially calibrated using aqueous solutions having known concentrations of the analyte salt (Ca$^{2+}$) and then each sample tested for calcium with a Ag/AgCl (3M NaCl) reference electrode. Each measurement was performed in triplicate. Cyclic voltammetry was carried out the thin film VISE with 20 mM Ca ionophore II in plasma with scan rates of 20 mV/s, 50 mV/s, 100 mV/s and 500 mV/s (FIG. 10a). The experiment was repeated using ISEs with differing film thicknesses of 1 µl, 2 µl and 4 µl and using a scan rate of 100 mV/s (FIG. 10(b)). The ISE with a film thickness of 4 µl, generated well defined reduction and oxidation peaks (but increasing the IR$_u$ and error in the measurement).

The 4 µl thin film VISE with 20 mM Ca ionophore II, at a scan rate of 100 mV s$^{-1}$ was used to test the Ca$^{2+}$ levels in blood and plasma and the results compared to the AEROSET 2 results as shown in Table 3.

The typical range for free Ca$^{2+}$ activity in plasma is 1.12-1.32 mM while the total Ca$^{2+}$ is 2.25-2.57 mM. All 9 samples tested on the AEROSET 2 are within the total Ca$^{2+}$ range when corrected for albumin concentration (Table 3). The Ca VISE gave free Ca$^{2+}$ levels at around 0.3 mM. As the blood was collected in lithium heparin tubes, the Ca$^{2+}$ activity would have been lowered by binding to heparin. The tubes were labelled as containing 119 IU of heparin, once corrected for this, the Ca$^{2+}$ levels are very close to the typical free Ca$^{2+}$ range (Table 3), correcting for calibration intercept shift would place all plasma, whole blood and frozen and thawed samples within the typical range.

TABLE 3

Comparison of AEROSET 2 results to those obtained using the VISE of the invention on whole blood, plasma and frozen/thawed plasma for free calcium, with corrections for albumin and heparin.

| Sample | Aeroset total Ca/mM | Aeroset Albumin Corrected Ca/mM | VISE Plasma average Ca/mM | Plasma average after heparin correction Ca/mM | Whole blood average Ca/mM | Whole blood average after heparin correction Ca/mM | Thawed Plasma average Ca/mM | Thawed Plasma average after heparin correction Ca/mM |
|---|---|---|---|---|---|---|---|---|
| ABA | 2.39 | 2.27 | 0.35 | 1.54 | — | — | — | — |
| ANA | 2.39 | 2.21 | 0.32 | 1.51 | — | — | — | — |
| ASA | 2.4 | 2.22 | 0.39 | 1.58 | — | — | 0.3717 | 1.56 |
| BDA | 2.37 | 2.27 | 0.37 | 1.56 | — | — | — | — |
| BGA | 2.43 | 2.25 | 0.19 | 1.38 | 0.3075 | 1.5 | — | — |
| BHA | 2.54 | 2.36 | 0.18 | 1.37 | — | — | — | — |
| BKA | 2.63 | 2.45 | 0.32 | 1.51 | 0.35385 | 1.54 | — | — |
| BRA | 2.29 | 2.23 | 0.42 | 1.61 | — | — | 0.3546 | 1.54 |
| BSA | 2.29 | 2.15 | 0.35 | 1.54 | — | — | — | — |

Example 11

Alternative Na+ sensor with Ag/AgCl reference solution

A sensor was produced in the same manner as Example 4 but using a Ag/AgCl saturated reference solution.

We claim:

1. A method for the quantitative determination of an ion in a fluid which comprises subjecting the fluid to voltammetry using a sensing electrode which comprises an electrically conducting support having a surface which is coated with a support matrix, the support matrix being a single layer containing (a) an electroactive species capable of being oxidised or reduced to form a charged species and (b) an ionophore, the support matrix having been obtained by drying a coating solution comprising the support matrix material, the electroactive species, and the ionophore;
   wherein the ionophore and the electroactive species are two different chemicals.

2. A method according to claim 1, wherein the support matrix additionally contains a solvent capable of at least partially dissolving the electroactive species and the ionophore.

3. A method according to claim 2, wherein the solvent is a plasticizer.

4. A method according to claim 2, wherein the solvent is an ionic liquid.

5. A method according to claim 4, wherein the ionic liquid is selected from 1-ethyl-3-methylimidazolium bis(trifluoromethane sulfonyl)amide (emim.tfsa), N-butyl-methylpyrrolidinium bis(trifluoromethanesulfonyl)amide (P14.tfsa) and trihexyl(tetradecyl)-phosphonium tris(pentafluoroethyl) trifluorophosphate (aph4.cph12).

6. A method according to claim 1, wherein the support matrix additionally contains an ionic salt which is substantially insoluble in the fluid.

7. A method according to claim 6, wherein the ionic salt is selected from tetra($C_4$-$C_{16}$ alkyl) ammonium salts.

8. A method according to claim 7, wherein the ionic salt is selected from tetrabutylammonium tetraphenylborate (TBATPB), tetrahexylammonium tetraphenylborate (THATPB), tetraheptyl ammonium perchlorate (THAClO$_4$) and tetraheptylammonium borate.

9. A method according to claim 1, wherein the electroactive species is hydrophobic.

10. A method according to claim 1, wherein the electroactive species undergoes reversible oxidation/reduction.

11. A method according to claim 1, wherein the electroactive species is selected from decamethylferrocene (DMFc), 1,1'-dimethylferrocene (DiMFc) and 7,7,8,8-tetracyanoquinodimethane (TCNQ).

12. A method according to claim 1, wherein the sensing electrode has at least one dimension of less than 50 μm.

13. A method according to claim 1, wherein the support matrix comprises a dielectric ink.

14. A method according to claim 1, which comprises contacting the fluid with the measuring electrode and with one or more further electrodes, supplying a time varying potential to the sensing electrode and determining the potential at which the resulting current is at a maximum.

15. A method according to claim 1, wherein the fluid is a body fluid selected from blood, urine and saliva.

16. A method according to claim 1, wherein the concentration of the ion in the fluid is from 0.1 μmol dm$^{-3}$ to 1.0 mol dm$^{-3}$, preferably from 0.1 mmol dm$^{-3}$ to 1.0 mol dm$^{-3}$.

17. An electrode comprising an electrically conducting support having a surface which is coated with a support matrix, the support matrix being a single layer containing (a) an electroactive species capable of being oxidised or reduced to form a charged species and (b) an ionophore, the support matrix having been obtained by drying a coating solution comprising the support matrix material, the electroactive species, and the ionophore;
   wherein the ionophore and the electroactive species are two different chemicals.

18. A device for the quantitative determination of an ion in a fluid which comprises an electrode as defined in claim 17 and one or more further electrodes.

19. A device according to claim 18, wherein the electrodes are present as conducting tracks on a single base.

20. A device according to claim 18, which comprises two or more electrodes, each such electrode comprising an electrically conducting support having a surface which is coated with a support matrix, the support matrix being a single layer containing (a) an electroactive species capable of being oxidised or reduced to form a charged species and (b) an ionophore, the support matrix having been obtained by drying a coating solution comprising the support matrix material, the electroactive species, and the ionophore;
   wherein the ionophore and the electroactive species are for each such electrode two different chemicals.

* * * * *

UNITED STATES PATENT AND TRADEMARK OFFICE
CERTIFICATE OF CORRECTION

PATENT NO.        : 7,799,204 B2                                                            Page 1 of 1
APPLICATION NO. : 11/665107
DATED             : September 21, 2010
INVENTOR(S)       : Jie Zhang et al.

It is certified that error appears in the above-identified patent and that said Letters Patent is hereby corrected as shown below:

Column 1, line 4:

Immediately after the title on page 1 insert:

--CROSS-REFERENCE TO RELATED APPLICATIONS

[0001]  This application is a national phase application based on PCT/GB2005/003988 filed on October 14, 2005, and also claims priority based on GB0423025.6 filed on October 15, 2004.

STATEMENT REGARDING FEDERALLY SPONSORED RESEARCH/DEVELOPMENT

[0002]  Not applicable--

Signed and Sealed this

Second Day of November, 2010

David J. Kappos
*Director of the United States Patent and Trademark Office*